United States Patent [19]

Hemmerich et al.

[11] Patent Number: 4,515,591
[45] Date of Patent: May 7, 1985

[54] DISPOSABLE SYRINGE CARTRIDGE FOR FLUID DELIVERY APPARATUS

[75] Inventors: Karl J. Hemmerich, Del Mar; Donald L. Millerd; Anthony B. Semedo, both of San Diego, all of Calif.

[73] Assignee: IVAC Corporation, San Diego, Calif.

[21] Appl. No.: 425,534

[22] Filed: Sep. 28, 1982

[51] Int. Cl.³ ............................................. A61M 5/20
[52] U.S. Cl. .................................. 604/152; 604/220; 604/222
[58] Field of Search .............................. 604/151–153, 604/218, 221, 222, 228, 208, 210, 220; 128/DIG. 12; 92/167, 187

[56] References Cited

U.S. PATENT DOCUMENTS

| | | | |
|---|---|---|---|
| 2,764,981 | 10/1956 | Helmer et al. | 604/210 |
| 3,934,586 | 1/1976 | Easton et al. | 604/208 |
| 3,993,061 | 11/1976 | O'Leary | 604/152 |
| 4,363,329 | 12/1982 | Raitto | 604/222 |
| 4,396,385 | 8/1983 | Kelly et al. | 604/152 |
| 4,399,778 | 8/1983 | Ancheta | 92/187 |

FOREIGN PATENT DOCUMENTS 1192787 5/1965 Fed. Rep. of Germany.
0011652 of 1874 United Kingdom.

Primary Examiner—C. Fred Rosenbaum
Assistant Examiner—Michelle N. Lester
Attorney, Agent, or Firm—Fulwider Patton Rieber Lee & Utecht

[57] ABSTRACT

A disposable syringe cartridge including a molded plastic cylinder having an open end and a closed end with inlet and outlet nipples integrally formed in the closed end, and a plastic piston head slidably received in the open end of the cylinder and pivotably connected to a plastic piston rod. The piston head utilizes a quad-type sealing ring providing a pair of adjacent sealing surfaces with the cylinder, and includes a square expansion flange rounded at each of its corners to conform in shape to the cylinder, with a rubber annular sealing boot extending between the open end of the syringe cylinder and the piston rod. A flange formed on the outer circumferential edge of the sealing boot is received over the open end of the cylinder and is captured by an annular cap that is ultrasonically welded to the cylinder, while a bead formed on the inner circumferential edge of the sealing boot is received in a groove defined by a pair of adjacent annular flanges formed on the piston rod. In an alternative embodiment, the piston head has two sealing rings, each carried adjacent an opposite end of the piston head, so that the sealing boot can be eliminated.

27 Claims, 12 Drawing Figures

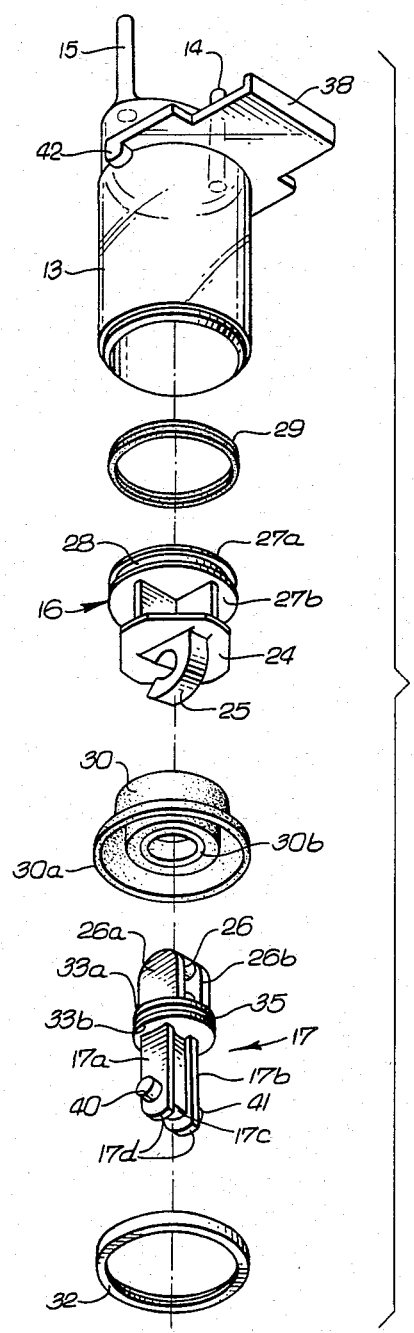

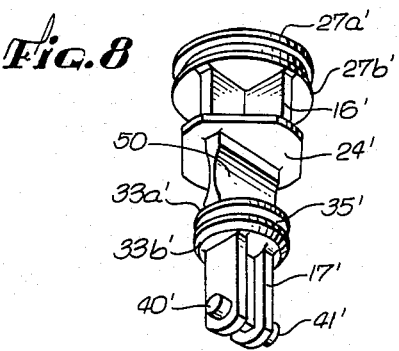
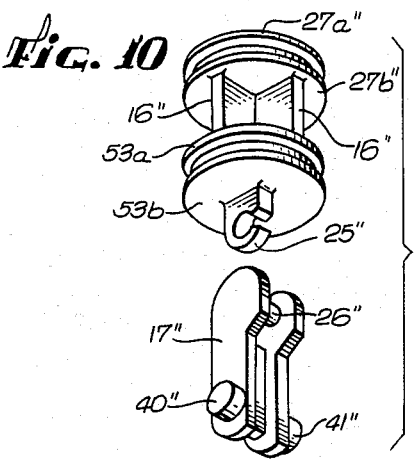
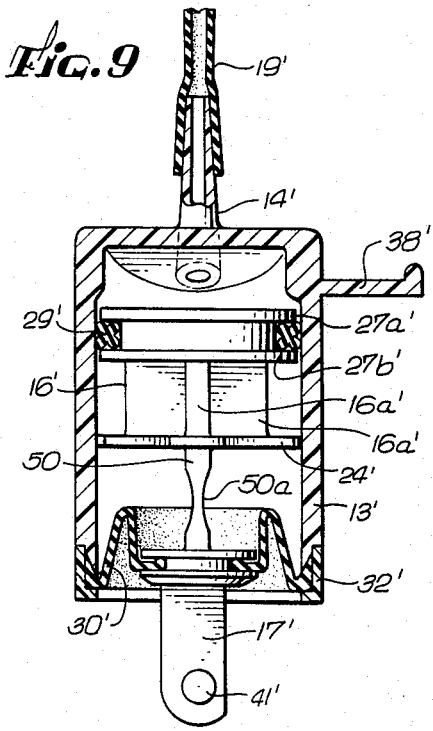
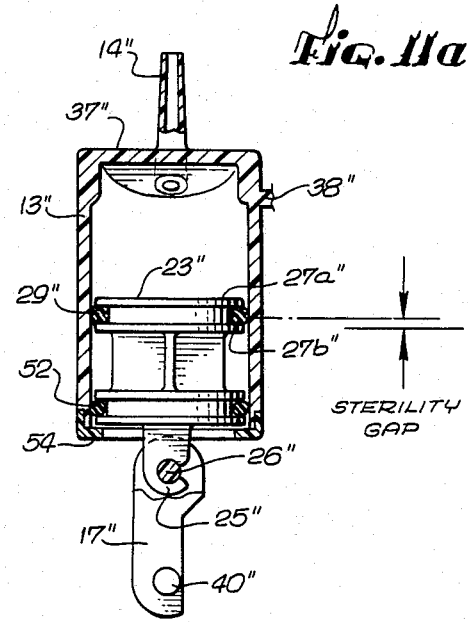
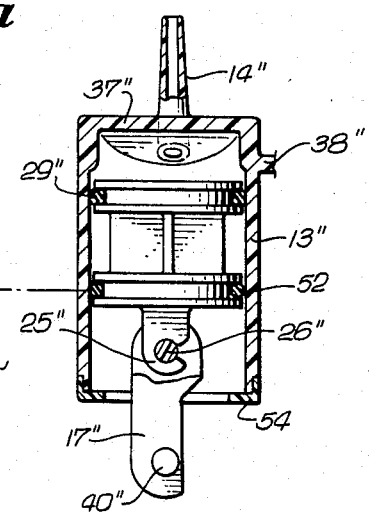

DISPOSABLE SYRINGE CARTRIDGE FOR FLUID DELIVERY APPARATUS

BACKGROUND OF THE INVENTION

This invention relates generally to improvements in fluid delivery systems and, more particularly, to a new and improved disposable syringe cartridge for a syringe pump.

The administration of parenteral fluids to human patients conventionally involves use of a solution administration set. The set typically is a disposable plastic product, and comprises a drip chamber adapted to be connected to a fluid source, a length of tubing extending from the chamber to the patient and a valve mechanism, such as a roller clamp on the tubing.

In recent years, a number of electrical monitoring systems, drop flow controllers and infusion pumps have been developed to accomplish the tasks of sensing and regulating the rate of fluid flow into the human body. One such development has been positive pressure infusion pumps of the syringe type, wherein a syringe having a very precise displacement volume is repeatedly filled and emptied on alternate syringe piston strokes during a combined "fill" and "pump" operational cycle, so that control of the rate at which the syringe is filled and emptied provides an accurate means for precise fluid volume delivery over a prescribed period of time. Such syringe pumps are essentially independent of drop flow inaccuracies introduced by I.V. administration sets and provide an overall solution to accurate and stable fluid volume delivery over long periods of time, at both high and low flow rates.

At the heart of the syringe pump is the syringe itself. Such syringes must be sufficiently rugged and reliable to enable repetitive fill and pump strokes over sustained periods of pump operation without leaking or admitting air or pathogens to the interior of the syringe. Where disposable syringes are involved, the syringe should preferably be of relatively simple economical construction, easily handled for insertion into and removal from the remainder of the pumping apparatus and should be mounted in such a fashion as to facilitate removal of air prior to startup. A prior disposable syringe cartridge designed to meet these and other requirements is shown and described in U.S. Pat. No. 3,993,061, issued Nov. 23, 1976, inventor Stephen H. O'Leary, which patent is assigned to the same assignee as the present application.

Basically, the disposable syringe cartridge disclosed in U.S. Pat. No. 3,993,061 includes a molded plastic cylinder having inlet and outlet nipples and defining an interior chamber adapted to slidably receive a plastic piston and integral piston rod. A rubber sealing cap overlies and encases the plastic piston, and defines a conical piston face. The sealing cap includes a pair of resilient annular ribs defining piston sealing rings, and further includes a limp diaphragm conical sealing boot. The dual, spaced apart sealing rings define two point contact along the longitudinal axis of the syringe to enchance axial alignment and stability of the piston and piston rod as the piston slides within the cylinder of the syringe, whereas the sealing boot at the base of the cylinder prevents the intake of air or pathogens through the bottom of the cylinder during repetitive strokes.

The disposable syringe cartridge of U.S. Pat. No. 3,993,061 itself embodies no valving structure, but includes a pair of intake and output I.V. tubes communicating with inlet and outlet nipples, respectively, of the syringe. The remainder of the pumping apparatus drives the syringe and repetitively and sequentially opens and closes the intake and output I.V. tubes by means of a pair of tube pinchers external to the syringe cartridge, the I.V. tubes alternating their opened and closed states, one tube pincher controlling each I.V. tube.

The inlet and outlet nipples of the syringe cartridge of U.S. Pat. No. 3,993,061 extend parallel to the longitudinal axis of the syringe, on opposite sides of the syringe. The interior surface of the cylinder defines, with the piston, a fluid chamber, and the cylinder surface above the piston is sloped upwardly towards the base of the outlet nipple, so that, when the longitudinal axis of the syringe is vertical, gas bubbles will tend to rise to the highest point of the cylinder and out through the outlet nipple for easy removal.

With the syringe cartridge of U.S. Pat. No. 3,993,061, an integral tab extends from the syringe cylinder and provides an operator handle for mounting and removing the syringe from the overall pumping apparatus. The end of the piston rod remote from the piston head is provided with mounting bosses to engage and be retained by a mounting shoe secured to the leading end of a linear drive shaft adapted to be coupled to the piston rod for driving the syringe through successive fill and pump strokes. A second pair of outwardly extending mounting bosses, parallel to the first set of mounting bosses on the piston rod, are integral with the syringe cylinder and are adapted to engage a pair of fixed guide and retaining slots provided in opposite walls of a syringe receiving compartment defined in the pump housing. The intake and output I.V. tubes from the syringe cartridge pass vertically over a pair of tube pincher blades and are clamped in position by a suitable tubing compartment access door which is appropriately latched.

Although the aforedescribed disposable syringe cartridge has performed generally satisfactorily, it was designed under the assumption that care would be taken by medical personnel to always properly install the cartridge assembly in the syringe pump. Specifically it was assumed that the longitudinal axis of the syringe cylinder would be aligned with the axis of reciprocation of the syringe driving system of the pump. It has been found, however, in practice that the syringe cartridge can be subject to misloading, which can result in misalignment of the syringe cylinder axis relative to the axis of reciprocation of the driving system. As a consequence, a fulcrum effect can be created in which the sealing rings of the piston head are forced away from the cylinder wall and fluid leaks past the piston head. Air or pathogens, or both can then be introduced into the syringe pumping chamber, which is of course undesirable.

It has further been found that the aforedescribed syringe cartridge can be improved in other respects, including the ease with which the cartridge can be sterilized, the sealing between the piston head and the cylinder wall, the design and attachment of the flexible boot, and the connection of the I.V. tubes to the syringe nipples, which can sometimes become dislodged.

Accordingly, it has been recognized that there is a need for an improved syringe cartridge that overcomes the foregoing problems, and yet maintains the desirable characteristics of being relatively simple, economical, reliable, stable and accurate. The present invention clearly fulfills this need .

SUMMARY OF THE INVENTION

Briefly, and in general terms, the present invention resides in a new and improved syringe cartridge that is relatively insensitive to misloading in the syringe pump and to resulting misalignment between the longitudinal axis of the syringe cylinder and the axis of reciprocation of the syringe drive system. The syringe cartridge of the present invention accommodates misloading without a fulcrum effect that leads to fluid leakage between the piston head and the cylinder. The present invention further allows easier sterilization, and provides, in various embodiments, improved sealing between the piston head and the cylinder wall, more secure attachment of a flexible sealing boot in the syringe assembly, and more secure attachment of a pair of intake and output I.V. tubes to inlet and outlet nipples, respectively, of the syringe.

More particularly, the disposable syringe cartridge of the present invention includes a hollow molded plastic cylinder that slidably receives a plastic piston head that is pivotally connected to a piston rod. The pivotal connection between the piston head and the piston rod prevents any lateral forces caused by misalignment from being transmitted through the piston rod to the piston head, thereby avoiding any undesirable fulcrum effect giving rise to fluid leakage. The piston head can carry a quad annular sealing ring, which has a substantially X-shaped radial cross-section providing two surfaces in sealing contact with the syringe cylinder for an improved seal. The cylinder with its integral nipples is formed from a material that is readily solvent bondable so that I.V. tubes may be solvent bonded to the nipples to eliminate any chance that either tube can become dislodged during use.

In one presently preferred embodiment of the invention, the piston head is defined at one end by a piston face that carries a first radially-outwardly extending annular flange and, at the opposite end, by a substantially square expansion flange having its four corners rounded for conformance with the shape of the syringe cylinder wall. The limited four-point contact of the expansion flange allows an easier exchange of sterilizing gas, while maintaining the piston head in axial alignment during reciprocation. The piston head further includes a second radially-outwardly extending annular flange adjacent to, but spaced from the first annular flange to define therebetween an annular groove into which the quad sealing ring is received. An annular sealing boot is affixed between the open end of the syringe cylinder and the piston rod to seal the bottom of the cylinder against entry of pathogens.

The piston head and the piston rod can be separate parts, and the pivotal connection between them can comprise an integral hook that depends from the bottom of the expansion flange and mates with a snap fit with a wrist pin that is integrally molded on the end of the piston rod. Alternatively, the piston head, the piston rod and the pivotal connection means can be integrally formed as a unitary structure of molded plastic. In that case, the connecting member has at limited flexibility, as provided for example by a relatively thin portion formed therein.

For more secure attachment of the annular sealing boot, its outer circumferential edge is provided with a flange adapted to be received over the open end of the syringe cylinder, and then an annular cap is received over and bonded, such as by ultrasonic welding, to the open end of cylinder with the boot edge firmly captured therebetween. A pair of parallel-spaced annular flanges are formed integrally with the piston rod to define an annular groove into which a bead on the inner circumferential edge of the sealing boot is received. The sealing boot is formed of a flexible, fluid impervious material in a bellows-like configuration, with sufficient material being provided so that the boot seals the open end of the syringe cylinder without stretching at any time during reciprocation of the piston head and the piston rod.

In a second preferred embodiment, the piston head is provided with two sealing rings, one sealing ring carried adjacent the piston face as in the first embodiment, and a second sealing ring carried between another pair of spaced-apart, radially-outwardly extending annular flanges formed at the bottom of the piston head. With this embodiment, the second sealing ring acts both as a back-up seal to the first seal ring and as a seal against pathogens and the like from the open end of the cylinder, so that no sealing boot is required. In this regard, this second embodiment is adapted for use with a syringe pump in which the length of the piston stroke of the piston drive system is no greater than the distance separating the first and second sealing rings carried by the piston head, so that the uppermost location achieved by the second sealing ring during piston upstroke is never higher than the lowermost location of the first sealing ring during piston downstroke. The result is maintenance of a sterile condition within the syringe cartridge, since the portion of the interior side wall of the cylinder that forms part of the fluid pumping chamber is never exposed to atmosphere at any time during reciprocation of the piston head. The amount by which the stroke is less than the separation between the sealing rings represents a sterility gap to assure that a sterile condition is maintained.

The above and other objects and advantages of the present invention will become apparent from the following more detailed description, when taken in conjunction with the accompanying drawings of illustrative embodiments.

DESCRIPTION OF THE DRAWINGS

FIG. 5 is an exploded perspective view of the main components of the first preferred embodiment of the syringe cartridge;

FIG. 6 is an enlarged fragmentary sectional view of the quad sealing ring carried by the piston head; and FIG. 7 is an enlarged fragmentary sectional view of the outer circumferential edge of the sealing boot and the annular cap that affixes the boot in place over the open end of the syringe cylinder;

FIG. 8 is a perspective view showing an alternative manner of forming the pivotal connection between the piston head and the piston rod in the first preferred embodiment of the invention;

FIG. 9 is a fragmentary sectional view of an assembled syringe cartridge embodying the alternative pivotal connection shown in FIG. 8;

FIG. 10 is a perspective view of a portion of a second preferred embodiment of the present invention, such portion comprising a piston head and a piston rod; and FIGS. 11a and 11b are fragmentary sectional views of the assembled syringe cartridge of the second preferred embodiment showing the piston head in the bottom dead center and top dead center positions, respectively.

DESCRIPTION OF THE PREFERRED EMBODIMENTS

Figure 1:
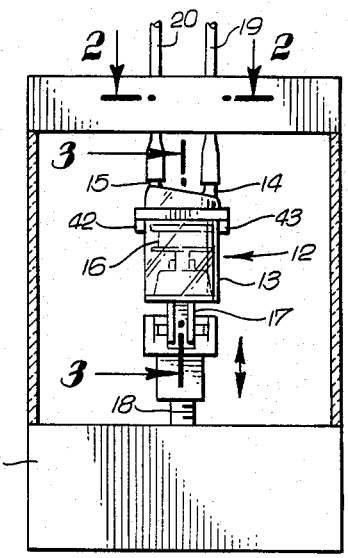
FIG. 1 is an elevational view showing a first preferred embodiment of a disposable syringe cartridge embodying the present invention, with a schematic representation being shown of a portion of a syringe pump drive system into which the syringe cartridge is installed.

Referring now to the drawings, there are shown, by way of example, the presently preferred embodiments of the invention. In the ensuing description, although reference is made to the term "I.V." normally meaning intravenous administration, it is to be understood that this is for convenience only, and the disposable syringe cartridge of the present invention is suitable for other forms of parenteral administration in addition to intravenous administration.

The system shown in FIG. 1 is a schematic representation of a portion of a syringe infusion pump 10 having a first preferred embodiment of a disposable syringe cartridge, indicated generally by reference numeral 12, installed or loaded therein for operation. The syringe cartridge 12 basically includes a molded plastic cylinder 13 having fluid inlet and outlet nipples 14, 15 integrally formed in a closed end, and a piston head 16 slidably received in an open end for reciprocation up and down along the axis of the cylinder by means of a piston rod 17 that extends between and is coupled to the piston head and a linear threaded drive shaft 18. In operation, the drive shaft will be alternately retracted and advanced by an appropriate motor drive and control system to first fill the syringe cylinder 13 with a precise volume of fluid from a source of fluid (not shown) via a length of I.V. tube 19 mounted over the inlet nipple 14, and to then pump that same precise volume of fluid from the syringe cylinder through the outlet nipple 15 and its associated I.V. tube 20 to the patient, respectively.

Figure 2:
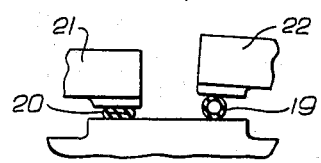
FIG. 2 is a fragmentary sectional view, taken substantially along the line 2—2 in FIG. 1, and illustrates the pincher valves external to the syringe cartridge.

As best seen in FIG. 2, the syringe infusion pump has a pair of tube pincher valves 21, 22, which are external to the syringe cartridge, and are selectively opened and closed at the appropriate times in the pumping cycle under the control of a suitable valve control system. Specifically, one valve 22 controls the fluid inlet and is open during the fill stroke to allow fluid to pass through the intake tube 19, while the other valve 21 is closed. During the pump stroke, the valve states are reversed so that the intake tube is pinched closed by the one valve 22 and the other valve 21 is open to allow fluid delivery to the patient through the outlet tube 20. The details of the syringe pump valving and motor control system do not form a part of the present invention, and will not be described further herein. Suitable systems are disclosed in U.S. Pat. Nos. 3,993,061; 3,994,294; and 4,137,913, all of which are assigned to the same assignee as the present application and are incorporated by reference herein.

Figure 3:
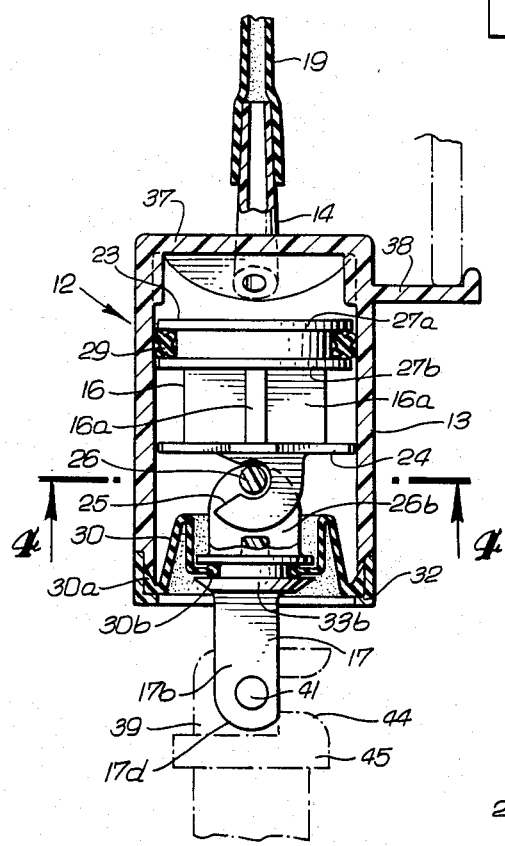
FIG. 3 is a fragmentary sectional view taken along the line 3—3 in FIG. 1, and illustrates the assembled syringe cartridge.

Referring now more particularly to FIGS. 3 and 5, it can be seen that the new and improved syringe cartridge 12 of the present invention is constructed to avoid any fulcrum effect caused by axial misalignment between the axis of the syringe cylinder 13 and the axis of reciprocation of the drive shaft 18 of the pump driving system. In this regard, the piston rod 17 is not integrally formed with the piston head 16 as a unitary structure, but rather there is a pivotal connection between the piston rod and the piston head. The piston head is defined at its oppostie ends by a piston face 23 and a square expansion flange 24. A coupling hook 25 is integrally formed with the piston head 16 to depend downwardly from the bottom of the expansion flange 24, and a cylindrical wrist pin 26 is integrally formed on the end of the piston rod 17, crosswise between a pair of integral spaced-apart, upstanding flanges 26a, b, and is received within the hook. The piston head and the piston rod, together with their respective connecting means, are molded of any suitable thermoplastic material, which inherently will be somewhat resilient, and this allows the opening in the hook 25 to be sized to receive the wrist pin 26 with a snap fit to form a simple, yet reliable coupling, the wrist pin then being free to pivot within the hook once fully received therein. By virtue of this pivotal connection, misalignment between the respective axes of the syringe cylinder and the drive shaft 18 is accommodated by the pivotal connection without transmitting any lateral misalignment forces to the piston head tending to skew it relative to the syringe cylinder and thereby cause fluid leakage.

Figure 4:
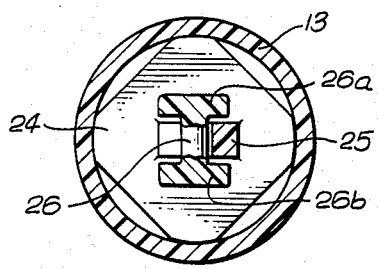
FIG. 4 is a sectional view taken along the line 4—4 in FIG. 3, and illustrates the pivotal connection between the piston head and the piston rod, as well as the square expansion flange of the piston head.

As best seen in FIGS. 4 and 5, the square expansion flange 24 is rounded at each of its four corners to conform in shape to the inside wall of the hollow syringe cylinder 13. The expansion flange 24, which forms the bottom of the piston head 16 and aids in maintaining it in proper axial orientation within the syringe cylinder, is joined to the piston force by four integral ribs 16a, which intersect at the longitudinal axis of the piston head. The limited four-point contact of the flange 24 with the cylinder 13 allows ETO sterilization gas to be exchanged more easily during the sterilization cycle, which results in a savings of both cost and time.

At the piston face 23, a pair of spaced-apart radially-outwardly extending integral annular flanges 27a, 27b are formed on the piston head 16 to define a groove 28 immediately below the piston face into which a sealing ring 29 is received. The sealing ring 29 is of the quad-type that is substantially X-shaped in radial cross-section so that the ring presents a pair of surfaces, rather than just a single surface, in sealing contact with the interior wall of the syringe cylinder 13 for an improved piston-head-to-cylinder seal (shown in enlargement in FIG. 6).

An annular sealing boot 30 extends between the open bottom end of the syringe cylinder 13 and the piston rod 17 to seal the syringe cylinder against pathogens and the like. The outer circumferential edge of the sealing boot 30 is provided with a flange 30a to overlie the open end of the syringe cylinder 13, and an annular cap 32, adapted to be received over the open end of the syringe cylinder, captures the edge of the sealing boot to firmly secure it in place, as shown in enlargement in FIG. 7. The cap 32 is designed to compress the sealing boot flange 31 and is ultrasonically welded to the syringe cylinder 13 to form a substantially fluid-tight seal.

A pair of spaced-apart radially-outwardly extending annular flanges 33a, b are integrally formed on the piston rod 17 to define an annular groove 35 into which a bead 30b formed along the inner circumferential edge of the annular sealing boot 30 is received. The bead 30b does not form a fluid-tight seal, and in fact is provided with a pair of gas vents (not shown) for gas sterilization purposes. It will be appreciated, however, that an effective seal against pathogens is maintained by virtue of the tortuous path between the annular flanges 33a, b and the bead 30b. The sealing boot 30 has a bellows-like configuration and is provided with sufficient material so that it seals the open end of the syringe cylinder 13 without stretching at any time during reciprocation of the piston head 16 and piston rod 17. The sealing boot 30 typically is fabricated of rubber to create a flexible and fluid impervious barrier.

The material from which the syringe cylinder 13 and integral nipples 14, 15 is fabricated is chosen not only for its cost, ease of manufacture and ability to withstand sterilization techniques, but also for its ability to take a solvent bond so that the I.V. tubes 19, 20 can be solvent welded to the nipples 14, 15, respectively. This ensures that the tubes will not become accidentally dislodged from the nipples after assembly, and particularly during use. Preferably the material for the syringe cylinder is a modified acrylic, vinyl, styrene or polycarbonate, although it will be appreciated that other materials would be suitable. With solvent bonding, the bond can be stronger than the tubing itself, so that the tubing would break before becoming dislodged from the nipple.

As with the prior syringe disclosed in U.S. Pat. No. 3,993,061, the inlet and outlet nipples 14, 15 of the syringe cylinder 13 extend parallel to the longitudinal axis of the syringe on opposite sides of the syringe, diametrically opposed from each other. The uppermost cylinder surface 37 above the piston head 16 is sloped upwardly, typically at an angle of approximately 10°, towards the base of the outlet nipple 15. Hence, when the longitudinal axis of the syringe is vertical, following installation into the pumping apparatus, gas bubbles will tend to rise to the highest point of the syringe cylinder 13 and pass out through the outlet nipple 15, for easy removal at some convenient access point in the output I.V. tube 20.

Also in a manner similar to the prior syringe cartridge, the syringe cartridge 12 of the present invention is constructed to cooperate with associated mounting means within the syringe compartment of the pump housing to facilitate simple and easy insertion of the cartridge into the pump housing while requiring the use of only one hand by the operator. In this regard, an integral tab 38 projects from the outer surface of the syringe cylinder 13 near the upper end of the cylinder, and thereby provides an operator handle for mounting and removing the syringe cartridge 12 from the pump housing in a manner described in further detail in U.S. Pat. No. 3,933,061. The piston rod 17 is molded in an H-shaped cross-section, defined by a pair of longitudinally extending, parallel flanges 17a, 17b, joined by an integral, coextensive cross-bar 17c. At the end of the piston rod 17 remote from the piston head 16, the longitudinal flanges 17a, 17b are partially cut-away to define surfaces 17d in order to provide clearance for insertion into a coupling shoe 39. In addition, this same end of the piston rod 17 is provided with a pair of integral, outwardly and oppositely extending, cylindrical mounting bosses 40, 41, one boss projecting perpendicularly outward from the outside face of the flange 17a, the other boss likewise projecting outward from the flange 17b. A second pair of outwardly extending mounting bosses 42, 43, parallel to the first set of mounting bosses 40, 41 on the piston rod 17, are integral with the syringe cylinder 13 and the tab 38 near the upper end of the cylinder.

As best observed in FIG. 3, the piston rod mounting bosses 40, 41 are adapted to engage and be retained by the mounting and coupling shoe 39, which is secured to the leading end of the linear drive shaft 18 adapted to be coupled to the piston rod 17 for driving the syringe cartridge 12 through successive fill and pump strokes. The coupling shoe 39 includes a pair of confronting, wide mouth guide slots 44 in upstanding flanges 45, disposed on opposite sides of the coupling shoe, and adapted to engage and guide the mounting bosses 40, 41 so that the syringe cartridge 12 can be inserted into the coupling shoe horizontally and then pivoted into a vertical orientation.

As described in more detail in the aforementioned patent, when the syringe cartridge 12 has been installed, the mounting bosses 40, 41 in the guide slots 44 prevent the syringe cartridge from being dislodged vertically, whereas the piston rod cut-away surfaces 17d received in the retention channel of the coupling shoe 39 prevent the cartridge from being dislodged horizontally. The mounting bosses 42, 43 of the syringe cylinder 13 are adapted to engage a pair of fixed guide and retaining slots provided in opposite walls of the syringe receiving compartment of the pump housing (not shown).

Referring now to FIG. 8, an alternative manner of forming the piston head, the piston rod and the pivotal connection therebetween is illustrated. As shown, a piston rod 17' and a piston head 16' are integrally formed as a unitary structure interconnected by a generally rectangular upstanding integral connecting plate 50. The connecting plate 50 is relatively thick at its opposite ends, where it joins the piston head 16' and the piston rod 17', and includes a reduced-thickness central portion 50a. The thickness of the central portion 50a is selected to provide a pivotal connection of at least limited flexibility to accommodate axial misalignment, while retaining sufficient strength to resist folding or collapsing in response to the compressive forces exerted on it during piston upstroke. The advantage of this design is greater simplicity and reduced cost of manufacture as a result of one less molding operation and elimination of an assembly step.

It will be appreciated that the thickness chosen for the central portion 50a of the connecting plate 50 will depend on many factors, including the material of which it is fabricated, the dimensions of the piston head and cylinder, and the viscosity of he fluid being pumped. The integral piston head, piston rod and connecting plate shown herein is molded of a material comprising polypropylene and a blowing agent. The connecting plate 50 is 0.100 inches thick at its thickest end portions and gradually reduces to 0.050 inches thick in its central portion 50a. Overall the connecting plate 50 is approximately 0.4 inches high and 0.5 inches wide, while the piston face 23' has a diameter of approximately 0.9 inches.

FIG. 9 shows an assembled syringe cartridge employing the integral piston head 16', piston rod 17', and connecting plate 50, and except for the features just described, is identical to the cartridge shown and described in connection with FIGS. 1–7. Corresponding reference numerals with prime marks therefore have been applied to the various elements illustrated in FIG. 9, and further description of its design and operation is unnecessary.

A second preferred embodiment of the disposable syringe cartridge of the present invention is shown in FIGS. 10 and 11. A piston head 16" is provided with two sealing rings, one sealing ring 29" carried adjacent the piston face 23" between a pair of spaced-apart, radially-outwardly extending integral annular flanges 27a", b", as with the first preferred embodiment. The second sealing ring 52 is carried adjacent the bottom of the piston head between a like pair of spaced-apart, radially-outwardly extending integral annular flanges 53a, b. The first sealing ring 29" is of the quad-type, while the second sealing ring 52 is a conventional O-ring.

The second sealing ring 52 functions as both a back-up seal to the first sealing ring 29" in the event of a fluid leak, and as a seal against atmosphere through the open end of the cylinder 13". In this regard, referring to FIGS. 11a and 11b, the second embodiment is adapted for use with a syringe pump in which the length of the piston stroke is no greater than the distance separating the first sealing ring 29" and the second sealing ring 52. As a result, that portion of the interior sidewall of the cylinder that is part of the fluid pumping chamber is never exposed to atmosphere at any time during reciprocation of the piston head. That is because the uppermost location achieved by the second sealing ring 52 during piston upstroke (FIG. 11b) is never higher than the lowermost location of the first sealing ring 29" during piston downstroke (FIG. 11a). By making the separation between the sealing rings somewhat greater than the stroke, a sterility gap is created to provide greater assurance of maintaining a sterile condition within the fluid pumping chamber. In the second preferred embodiment, the sterility gap is a minimum of several thousandths of an inch.

An advantage of this design is again reduced cost as the flexible sealing boot on the open end of the cylinder may be eliminated, although an annular retainer cap 54, similar to the sealing boot cap 32 of the first embodiment, is provided to retain the piston head 16" in the cylinder 13" of the assembled cartridge.

The syringe cartridge of the second preferred embodiment is otherwise the same as the first embodiment, and corresponding references with double-prime marks have been applied so that further description will not be needed. It should be noted, however, that although the piston head and the piston rod of the second embodiment are shown as separate parts, they could be integrally formed with a flexible connecting member as shown in FIG. 8.

The present invention satisfies the need for an improved and yet relatively simple, economical, reliable, stable and accurate disposable syringe cartridge.

It will be apparent from the foregoing that, while particular forms of the invention have been illustrated and described, various modifications can be made without departing from the spirit and scope of the invention. Accordingly, it is not intended that the invention be limited, except as by the appended claims.

We claim:

1. For use in a syringe pump, a disposable plastic syringe cartridge, comprising:
   a hollow cylinder having an open end and a closed end, said cylinder having a pair of inlet and outlet nipples projecting from said closed end of said cylinder, each of said nipples adapted for connection to an I.V. tube;
   a piston head slidably received within said cylinder;
   a sealing ring disposed around said piston head for forming a circumferential sealing relationship with said cylinder;
   a piston rod for reciprocating said piston head along the longitudinal axis of said cylinder;
   means for pivotally connecting one end of said piston rod to said piston head; and
   means for engaging the other end of said piston rod to the mounting means of a piston drive system.

2. Apparatus as set forth in claim 1, and further including an annular sealing boot formed of a flexible and fluid impervious material, the outer circumferential edge of said boot affixed to said open end of said cylinder, and the inner circumferential edge of said boot affixed to said piston rod, said sealing boot having sufficient material between its outer and inner circumferential edges to seal said open end of said cylinder without stretching at any time during reciprocation of said piston head.

3. Apparatus as set forth in claim 2, and further including:
   an annular cap received over and bonded to said open end of said cylinder with said outer circumferential edge of said boot captured between said annular cap and said open end of said cylinder to secure said boot in place.

4. Apparatus as set forth in claim 2, wherein said piston rod further includes a pair of parallel spaced-apart integral annular flanges between which said inner circumferential edge of said boot is received.

5. Apparatus as set forth in claim 1, wherein said sealing ring disposed around the circumference of said piston head comprises a quad sealing ring having a substantially X-shaped radial cross-section such that said sealing ring has a pair of adjacent surfaces in sealing contact with said cylinder.

6. Apparatus as set forth in claim 1, wherein said piston head and said piston rod are formed as separate parts, and further wherein said means for pivotally connecting said piston rod to said piston head comprises an integral hook depending from said piston head and an integral wrist pin formed in said one end of said piston rod, said wrist pin receivable in said hook with a snap fit.

7. Apparatus as set forth in claim 1, wherein said piston head and said piston rod are integrally formed as a unitary structure, and further wherein said means for pivotally connecting said piston rod to said piston head comprises an integral connecting member having at least limited flexibility.

8. Apparatus as set forth in claim 7, wherein said piston head, said piston rod and said integral connecting member are molded plastic, and further wherein said integral connecting member includes a relatively thin portion imparting flexibility to said member.

9. Apparatus as set forth in claim 1, and further including:
   an I.V. tube solvent-bonded to each of said nipples.

10. For use in a syringe pump, a disposable plastic syringe cartridge, comprising:
    a hollow cylinder having an open end and a closed end, said cylinder having a pair of inlet and outlet nipples projecting from said closed end of said cylinder, each of said nipples adapted for connection to an I.V. tube;
    a piston head slidably received within said cylinder;

a sealing ring disposed about the circumference of said piston head for forming a circumferential sealing relationship with said cylinder;

a piston rod for reciprocating said piston head along the longitudinal axis of said cylinder;

means for pivotally connecting one end of said piston rod to said piston head;

means for engaging the other end of said piston rod to the mounting means of a piston drive system; and means for forming a flexible seal between the open end of said cylinder and said piston rod to seal said cylinder at all times during reciprocation of said piston head.

11. Apparatus as set forth in claim 10, wherein the opposite ends of said piston head are defined respectively by a piston face and a substantially square expansion flange that is spaced from and parallel to said piston face, the four corners of said piston face being rounded for conformance with the shape of said cylinder.

12. Apparatus as set forth in claim 10, wherein said sealing ring disposed about the circumference of said piston head comprises a quad sealing ring having a substantially X-shaped radial cross-section such that said sealing ring has a pair of adjacent surfaces in sealing contact with said cylinder.

13. Apparatus as set forth in claim 12, wherein said piston head has a pair of parallel spaced-apart integral annular flanges between which said sealing ring is disposed.

14. Apparatus as set forth in claim 10, wherein said piston head and said piston rod are formed as separate parts, and further wherein said means for pivotally connecting said piston rod to said piston head comprises an integral hook depending from said piston head and an integral wrist pin formed in said one end of said piston rod, said wrist pin receivable in said hook with a snap fit.

15. Apparatus as set forth in claim 10, wherein said piston head and said piston rod are integrally formed as a unitary structure, and further wherein said means for pivotally connecting said piston rod to said piston head comprises an integral connecting member having at least limited flexibility.

16. Apparatus as set forth in claim 15, wherein said piston head, said piston rod and said integral connecting member are molded plastic, and further wherein said integral connecting member includes a relatively thin portion imparting flexibility to said member.

17. Apparatus as set forth in claim 10, and further including:

an I.V. tube solvent-bonded to each of said nipples.

18. For use in a syringe pump, a disposable plastic syringe cartridge, comprising:

a hollow cylinder having an open end and a closed end, said cylinder having a pair of inlet and outlet nipples projecting from said closed end of said cylinder, each of said nipples adapted for connection to an I.V. tube;

a piston head slidably received within said cylinder;

a quad sealing ring disposed about the circumference of said piston head for forming a circumferential sealing relationship with said cylinder, said quad sealing ring having a substantially X-shaped radial cross-section such that said sealing ring has a pair of adjacent surfaces in sealing contact with said cylinder;

a piston rod for reciprocating said piston head along the longitudinal axis of said cylinder;

means for pivotally connecting one end of said piston rod to said piston head;

means for pivotally engaging the other end of said piston rod to the mounting means of a piston drive system; and an annular sealing boot formed of a flexible and fluid impervious material, the outer circumferential edge of said boot received over and affixed to said open end of said cylinder, and the inner circumferential edge of said boot affixed to said piston rod, said sealing boot having sufficient material between its outer and inner circumferential edges to seal said open end of said cylinder without stretching at any time during reciprocation of said piston head.

19. Apparatus as set forth in claim 18, and further including:

an annular cap received over and bonded to said open end of said cylinder with said outer circumferential edge of said boot captured between said annular cap and said open end of said cylinder to secure said boot in place.

20. Apparatus as set forth in claim 19, wherein said piston rod further includes a pair of parallel spaced-apart integral annular flanges between which said inner circumferential edge of said boot is received.

21. Apparatus as set forth in claim 18, wherein the opposite ends of said piston head are defined respectively by a piston face and a substantially square expansion flange that is spaced from and parallel to said piston face, the four corners of said expansion flange being rounded for conformance with the shape of said cylinder.

22. Apparatus as set forth in claim 21, wherein said piston head further includes a pair of parallel spaced-apart integral annular flanges between which said sealing ring is disposed.

23. Apparatus as set forth in claim 18, wherein said piston head and said piston rod are formed as separate parts, and further wherein said means for pivotally connecting said piston rod to said piston head comprises an integral hook depending from said piston head and an integral wrist pin formed in said one end of said piston rod, said wrist pin receivable in said hook with a snap fit.

24. Apparatus as set forth in claim 18, wherein said piston head and said piston rod are integrally formed as a unitary structure, and further wherein said means for pivotally connecting said piston rod to said piston head comprises an integral connecting member having at least limited flexibility.

25. Apparatus as set forth in claim 24, wherein said piston head, said piston rod and said integral connecting member are molded plastic, and said integral connecting member includes a relatively thin portion imparting flexibility to said member.

26. Apparatus as set forth in claim 18, and further including:

an I.V. tube solvent-bonded to each of said nipples.

27. For use in a syringe pump, a disposable plastic syringe cartridge, comprising:

a hollow cylinder having an open end and a closed end, said cylinder having a pair of inlet and outlet nipples projecting from said closed end of said cylinder, each of said nipples adapted for connection to an I.V. tube;

a piston head slidably received within said cylinder;

a sealing means disposed around the circumference of the piston head comprising a quad sealing ring having a substantially X-shaped radial cross section such that the sealing ring has a pair of adjacent surfaces in sealing contact with said cylinder;

a piston rod for reciprocating said piston head along the longitudinal axis of said cylinder;

means for pivotally connecting one end of said piston rod to said piston head; and means for engaging the other end of said piston rod to the mounting means of a piston drive system.

* * * * *